(12) United States Patent
Single et al.

(10) Patent No.: US 6,463,932 B1
(45) Date of Patent: *Oct. 15, 2002

(54) MALE URINARY INCONTINENCE CONTROL DEVICE

(76) Inventors: Charles H. Single, 3769 Bridle Pass, Ann Arbor, MI (US) 48108; John D. Cochrane, III, 1530 Edinborough, Ann Arbor, MI (US) 48104

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/507,455

(22) Filed: Feb. 22, 2000

Related U.S. Application Data (63) Continuation-in-part of application No. PCT/US99/03836, filed on Feb. 19, 1999.

(51) Int. Cl.[7] .................................................. A61F 5/48
(52) U.S. Cl. ................................. 128/885; 128/DIG. 25
(58) Field of Search ............................... 128/846, 885, 128/886, DIG. 25; 600/38–40

(56) References Cited

U.S. PATENT DOCUMENTS

| | | | | |
|---|---|---|---|---|
| 3,147,754 A | * | 9/1964 | Koessler | ..................... 128/885 |
| 3,203,421 A | * | 8/1965 | Bialick | |
| 3,866,611 A | * | 2/1975 | Baumrucker | |
| 4,428,365 A | * | 1/1984 | Hakky | ......................... 128/885 |
| 4,800,900 A | | 1/1989 | French | |
| 4,942,886 A | | 7/1990 | Timmons | |
| 5,184,629 A | | 2/1993 | Erickson et al. | |
| 5,336,157 A | | 8/1994 | Hale | |
| 5,526,803 A | * | 6/1996 | Kelly | |
| 5,571,125 A | | 11/1996 | Chadwick | |
| 5,795,334 A | | 8/1998 | Cochrane, III | |

* cited by examiner

Primary Examiner—Michael A. Brown
(74) Attorney, Agent, or Firm—Brinks Hofer Gilson & Lione (57) ABSTRACT

A male urinary incontinence control device (10) including a first element (12) for applying preferential pressure to the penis shaft (14) between the lateral superficial veins (18) and the central dorsal vascular group (20), and a second element (28) for applying pressure ventrally to the penis shalt (14) at the urethra (30) and the corpus spongiosum (32) thereby substantially or completely closing the urethra (30) and preventing or limiting the flow of urine through the urethra (30). Both longitudinally and transversely oriented lower bolsters are disclosed.

4 Claims, 9 Drawing Sheets

MALE URINARY INCONTINENCE CONTROL DEVICE

REFERENCE TO RELATED APPLICATION

This application is a continuation-in-part of international application number PCT/US99/03836, filed Feb. 19, 1999 (pending).

BACKGROUND OF THE INVENTION

1. Technical Field

This invention generally relates to medical appliances and, more particularly, to a device used to control urinary incontinence of a male patient.

2. Discussion

Male urinary incontinence is a long-recognized medical condition which can pose an embarrassment to men whose natural urethral valve or sphincter is no longer capable of controlling the flow of urine from the bladder. Urinary incontinence can arise from a variety of causes, including disease, surgery, neurological dysfunction, malformation of the urethral valve, physical deterioration accompanying advancing age, and other causes. Externally applied absorbent pads and internal catheters connected to collection bags are currently used as solutions to the problem of incontinence. Each of these solutions ultimately entails the external collection of the urine which escapes the bladder. Unfortunately, collection devices such as these can often be uncomfortable, inconvenient, unsanitary, offensive, unreliable and even inadequate during use.

A variety of other devices are known for more actively regulating or controlling male urinary incontinence, rather than merely externally capturing or collecting urine. Some of these other devices include clamps or valves which are surgically implanted, positioned around and compressing the urethra. The clamp or valve is actuated in one way or another to permit the flow of urine through the urethra. These invasive devices have several drawbacks. The most significant of these drawbacks is the risk and cost associated with performing the implant surgery.

Other commonly employed devices for the control of incontinence are non-invasive devices or appliances which include a strap, band, cuff, clamp, cradle, or other member which encircles the penis shaft. A device of this type is positioned about and tightened around the penis shaft until sufficient pressure is applied to the urethra and the corpus spongiosum to substantially or completely close the urethra. The device is loosened or removed to permit the flow of urine through the urethra when appropriate.

A wide variety of non-invasive type devices are known in the art. Such devices can include single or plural members which are flexible or rigid. Some devices include a projection intended to lie beneath the urethra and corpus spongiosum to apply a sealing pressure to the urethra and corpus spongiosum. This projection can be rigid or resilient, or can even be an inflatable sac. This last construction is shown in U.S. Pat. No. 4,800,900 (issued to G. J. French on Jan. 31, 1989, and herein after referred to as the '900 patent'), and is particularly advantageous in that deflation of the sac reduces the pressure applied to the urethra sufficiently to allow urination without requiring removal of the device from the penis shaft.

Devices of the encirclement type usually permit sufficient tightening of the device around the penis shaft to prevent or substantially reduce the leakage of urine through the urethra. Unfortunately, sufficient tightening of the encirclement type device almost universally results in the application of an unacceptable and sometimes painful amount of pressure to tissues other than the urethra and corpus spongiosum. In particular, virtually all devices of this type apply undue pressure to the superficial dorsal vein, the deep dorsal veins, and the dorsal arteries and nerves. This grouping of veins, arteries, and nerves will be referred to as the central dorsal vascular group throughout the present disclosure.

Devices of this general type are often subject to other drawbacks as well. Some are difficult to properly position on the penis shaft. Others are relatively complex in construction, and therefore relatively expensive to manufacture. Some provide poor adjustability to the particular patient using them. Further, wearing many of these devices can be quite uncomfortable, and virtually impossible to withstand for more than a few hours at a time.

In light of the above, a need appears within the industry for a device for controlling male urinary incontinence which avoids applying undue pressure to the superficial dorsal vein, the deep dorsal vein, the lateral superficial veins and the dorsal arteries and nerves of the penis shaft, while ensuring that sufficient pressure is applied to the urethra and the corpus spongiosum to prevent or substantially reduce leakage from the urethra. A need also exists for a device which provides for a relatively precise selection of the dorsally and ventrally applied pressures. The needed device would avoid inflicting pain, trauma and/or damage to the skin and underlying tissues of the penis shaft when used. It would be desirable for such a device to be comfortably worn by the patient for an entire day without removal, except for removal to permit urination. It would further be desirable for such a device to be relatively inexpensive in construction, and relatively easy both to properly position on the penis shaft, and to remove for urination.

SUMMARY OF THE INVENTION

The foregoing problems are solved and a technical advance is achieved in an illustrative male urinary incontinence control device which is particularly useful in that it is more comfortable to wear and use than prior devices, yet provides adequate closure of the urethra so as to prevent or substantially reduce leakage of urine through the urethra. The present invention can most simply be considered as an improvement in a strap, band, cuff, clamp or cradle type incontinence control device, the improvement comprising the inclusion of a means (such as a pair of projections or bolsters) which applies pressure preferentially at the specific areas between the lateral superficial veins and the superficial dorsal vein, the deep dorsal vein and the dorsal arteries and nerves. The superficial dorsal vein, the deep dorsal vein and the dorsal arteries and veins can, for practical purposes, be considered comprised within a single group located very near the top center of the dorsal surface of the penis shaft. As previously mentioned, this grouping will be referred to as "the central dorsal vascular group". Thus, the control device of the present invention includes a means which applies pressure preferentially at the specific areas between the lateral superficial veins and the central dorsal vascular group.

"Preferentially" (or "preferential") should be understood as meaning that the pressure applied to the penis shaft by the pressure-applying means is greater at these specific areas than the pressure applied elsewhere to the penis shaft, save perhaps for the pressure applied ventrally to the urethra and the corpus spongiosum. The device of the present invention also applies pressure ventrally to the urethra and the corpus spongiosum, however, with the result that the urethra can be closed or substantially closed, while undue pressure on the superficial dorsal vein, the lateral superficial veins, the deep dorsal vein and the dorsal arteries and nerves is avoided. "Substantially" means that leakage through the urethra when the device is in place is reduced to as low as about one to six percent of the patient's daily urine output, typically only about 36 to 75 ml and 20 to 40 ml depending on the embodiment of the device, of a daily outflow of about 1200 to 1500 ml.

This improvement is preferably embodied in a male urinary incontinence control device in which three projections or bolsters are carried on arms of a generally C-shaped resilient member. The words "projections" and "bolsters" are equivalent for the purposes of the invention, and "bolsters" should be understood to be a generic term, encompassing not only "projections," but also all equivalents of them which extend from the device towards the penis shaft, or which otherwise provide for the preferential application of pressure. The arms of the resilient member are joined by, and preferably unitarily formed with, a spring means. The arms are pivoted towards one another and held in a position by a clip or closure means disposed substantially opposite the spring. Two of the bolsters abut the penis shaft dorsally in the specific areas mentioned above, while the third bolster abuts the penis shaft ventrally at the corpus spongiosum and the urethra. The projections or bolsters are preferably composed of a material softer than or equal to that of the resilient member. Further, the third or ventral bolster can be the inflatable sac (25) disclosed in the '900 patent, cited above. The entirety of the disclosure of the '900 patent is expressly incorporated herein by reference.

The present invention is particularly advantageous in that it avoids applying undue pressure to the lateral superficial veins and the central dorsal vascular group while ensuring that sufficient pressure is applied to the urethra and the corpus spongiosum to prevent or substantially reduce leakage through the urethra. Unexpectedly, the positioning of the dorsal pressure-applying means of the control device of the present invention avoids the application of undue pressure to the deep arteries in the corpi cavernosa, even when the applied pressure is sufficient to close or substantially close the urethra. This decreases the risk of discomfort during use of the device of the present invention. The device permits a relatively precise selection of the dorsally and ventrally applied pressures by adjusting the spring means and by correctly selecting the length of the closure means. The present invention substantially reduces or avoids the pain, trauma and/or damage to the skin and underlying tissues of the penis shaft during use when compared to the use of other encirclement type devices. The device of the present invention can be comfortably worn by the patient for an entire day (for example, as much as eighteen hours) without removal, except, of course, for removal to permit urination. The control device of the present invention is relatively inexpensive in construction, and the device is relatively easy both to position properly on the penis shaft, and to remove for urination. Indeed, when the device incorporates a sac similar to the type disclosed in U.S. Pat. No. 4,800,900, the device need not be removed for urination at all.

One aspect the present invention is directed to a male urinary incontinence control device having a first means for applying preferential pressure to the penis shaft at areas between the lateral superficial veins and the central dorsal vascular group, and a second means for applying pressure ventrally to the penis shaft at the urethra and the corpus spongiosum. The second pressure-applying means can simply be the ventral portion of any strap, band, cuff, clamp, cradle or the like which engages the penis shaft and applies pressure for closing the urethra. Preferably, however, the first and second pressure-applying means each comprise an arm carrying on them the projections or bolsters mentioned above. Also, each bolsters of the top can include a slit receiving the associated arm through it, so that the bolsters are movable along the arm on which they are carried. This permits precise fitting of the device to the diameter of the penis shaft of the particular patient wearing it.

Alternatively, the ventral bolster can include an inflatable sac. In such a case, the device of the present invention preferably further includes the valve and syringe assemblies associated with the sac as disclosed in the '900 patent. Preferably, however, the shape of the sac in the present invention will be somewhat different from the shape shown in the referenced patent. In particular, the sac in the present invention will be relatively longer in one direction (in a direction parallel or transverse to the urethra), and relatively shorter in its other direction.

The dorsal and ventral arms of the first and second pressure-applying means are preferably unitarily and continuously formed with a spring means which connects them, generally yielding a C-shaped device. Also, the arms and the spring means are preferably formed as a leaf with ramped edges, composed of stainless steel or a medical grade plastic material.

In a second aspect, the present invention is directed to a device of the type disclosed above, and specifically including a particular combination of elements. More particularly, in its second aspect the present invention is directed to a male incontinence control device having a first means for applying preferential pressure to the penis shaft at areas between the lateral superficial veins and the central dorsal vascular group, a second means for applying pressure ventrally to the penis shaft at the urethra and the corpus spongiosum, and a spring means connecting the first and second pressure-applying means. The spring means being unitarily formed with the first and second pressure-applying means, wherein the first pressure-applying means includes a dorsal arm and a pair of dorsal bolsters on the dorsal arm facing the second pressure-applying means, the dorsal bolsters being movable along the dorsal arm, and wherein the second pressure-applying means includes a ventral arm and a ventral bolster on the ventral arm facing the first pressure-applying means. In this aspect, the dorsal and ventral arms of the first and second pressure-applying means, and the spring means, are continuously formed as a C-shaped leaf composed of stainless steel or a plastic, wherein the first pressure-applying means includes a relief means located over the dorsal arteries and nerves, the relief means being a portion of the dorsal arm of the first pressure-applying means spaced away from the dorsal arteries and nerves, and wherein the dorsal bolsters each include a slit through which the dorsal arm is received. The ventral bolster of the second aspect includes either a slit through which the ventral arm is received, or an inflatable sac, and the device further includes a clip connectable to the first and second arms opposite the spring means, the clip limiting movement of the first and second arms away from one another or the penis shaft.

In a further aspect of the invention, a variant off of either aspect mentioned above, the second pressure-applying means is specifically oriented transverse to the penis shaft and urethra. As such, the second pressure-applying means may or may not include a bolster oriented along an arm which carries it.

In still another aspect of the invention, and being another variant of the above mentioned aspects, at least one of the first and second pressure-applying means, comprised of an arm, is of a modified cross-sectional shape. In particular, the cross-sectional shape of at least a portion of the arm is of a modified "V-shape". Notably, the apex or point of the V-shape is toward the penis shaft; when the device is applied thereto.

In yet another aspect, the present invention is directed to an improvement in a strap, band, cuff, clamp or cradle type urinary incontinence control device attachable to the penis shaft and applying pressure ventrally to at least the urethra and corpus spongiosum, the improvement being means on the device for applying preferential pressure to the penis shaft at areas between the lateral superficial veins and the central dorsal vascular group, such that adequate pressure to substantially reduce leakage of urine through the urethra can be applied without unduly interfering with the flow of blood in the penis shaft.

Again, as mentioned above, the incontinence control device of the present invention possesses several significant advantages, most notably that it avoids the undue application of pressure to the lateral superficial vein and the central dorsal vascular group (the superficial dorsal veins, the deep dorsal vein, and the dorsal arteries and nerves) while permitting complete or substantially complete closure of the urethra, thereby comfortably preventing significant leakage of urine from the bladder.

BRIEF DESCRIPTION OF THE DRAWINGS

The various advantages of the present invention will become apparent to one skilled in the art upon reading the following specification and by reference to the accompanying drawings, wherein like reference characters refer to like parts throughout the several views, and in which:

FIG. 19 is a bottom perspective view of the biasing member of another embodiment of the present invention and FIG. 19B is an end view thereof illustrating in detail the projection on the lower arm;

DETAILED DESCRIPTION OF THE PREFERRED EMBODIMENTS

Figure 1:
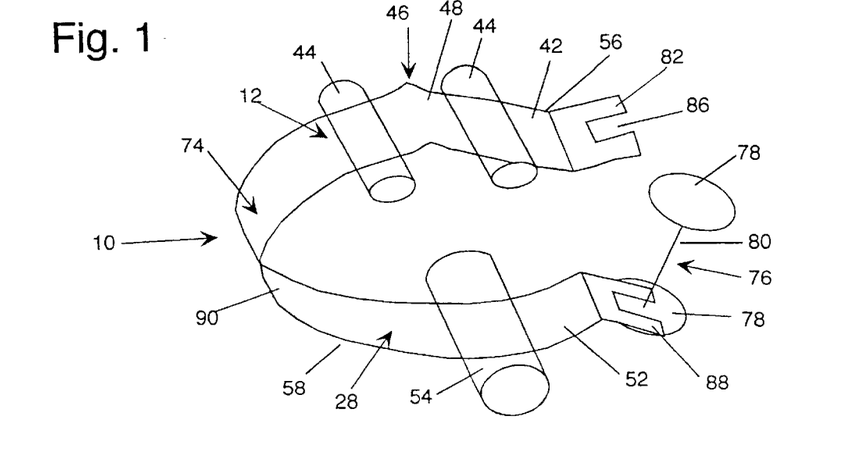
FIG. 1 is a perspective view of a device made in accordance with the teachings of the present invention.
Figure 2:
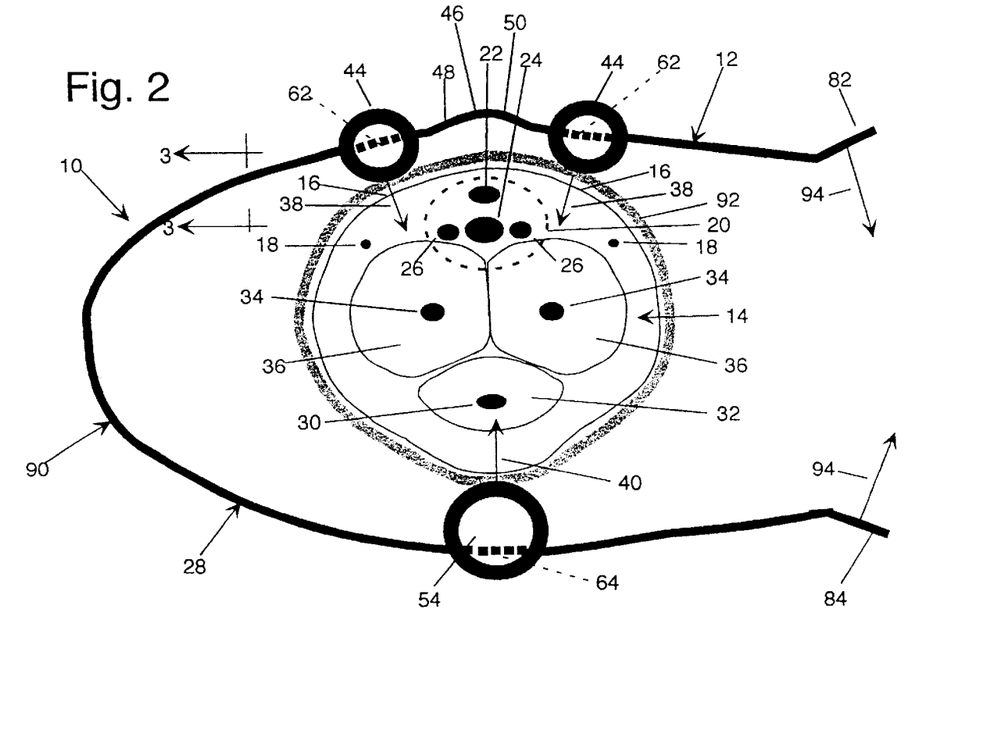
FIG. 2 is a side view of the embodiment in FIG. 1 prior to application of the device to the penis shaft.

With reference first to FIGS. 1 and 2, a male urinary incontinence control device 10 according to the present invention is shown. The control device 10 includes a first means 12 for applying preferential pressure to the penis shaft 14 at areas 16 between the lateral superficial veins 18 and the central dorsal vascular group 20. The central dorsal vascular group 20 is used in the present description to include the superficial dorsal vein 22, the deep dorsal vein 24 and the dorsal arteries and nerves 26. The control device 10 also includes a second means 28 for applying pressure ventrally to the penis shaft 14 at the urethra 30 and the corpus spongiosum 32. The first and second pressure-applying means 12 and 28 cooperate to apply sufficient pressure to the penis shaft 14 to close or substantially close the urethra 30 and prevent leakage, while avoiding the application of undue pressure to the penis shaft 14 at the lateral superficial veins 18, the central dorsal vascular group 20, and the deep arteries 34 in the corpi cavernosa 36. The pressure applied dorsally by the first pressure-applying means 12 is designated in FIG. 2 by the arrows 38, while the pressure applied ventrally by the second pressure-applying means 28 is designated by the arrow 40.

The first pressure-applying means 12 preferably includes a dorsal arm 42 and a spaced pair of dorsal bolsters 44 movably carried on the dorsal arm 42. The dorsal bolsters 44 face and project towards the second pressure-applying means 28. The first pressure-applying means 12 preferably also includes a relief means 46 located over the central dorsal vascular group 20. The relief means 46 encompasses a short portion 48 of the dorsal arm 42 which is located above the central dorsal vascular group 20. This short portion 48 is formed as a bend 50 in the dorsal arm 42 which has a much smaller radius of curvature than that (if any) of the dorsal arm 42. This causes the short portion 48 to be raised up and away from the surface of the penis shaft 14, thereby reducing the possibility of applying undesired pressure to the central dorsal vascular group 20. The dorsal bolsters 44 are positioned on each side of the short portion 48.

Figure 3:
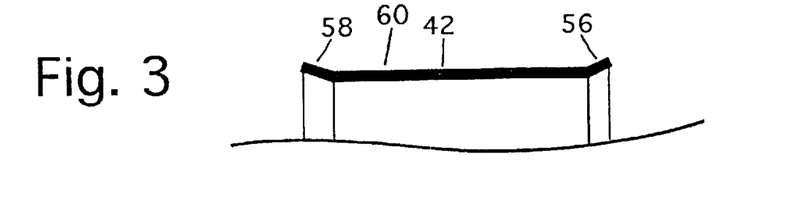
FIG. 3 is a cross-sectional view taken along line 3—3 of FIG. 2.

The second pressure-applying means 28 preferably includes a ventral arm 52 and a ventral bolster 54 movably carried on the ventral arm 52. The ventral bolster 54 faces and projects towards the first pressure-applying means 12. The dorsal arm 42 includes edges 56 and 58 which are angled or ramped from a normal plane 60 of the arm 42 as shown in FIG. 3. While not shown, the ventral arm 52 also includes edges 56 and 58 with similar angles or ramped features. The edges 56 and 58 are angled to prevent injury to the penis shaft 14 while applying or wearing the control device 10.

The dorsal bolsters 44 and the ventral bolster 54 can be formed in any convenient shape suited to provide the pressures indicated above. The ventral bolster 54 of the preferred embodiment is generally firmer than the penis shaft 14, while the dorsal bolsters 44 of the preferred embodiment are generally equal to or softer than the penis shaft 14. More particularly, the firmness of the dorsal bolsters 44 should match that of the penis shaft 14 when wrapped in the manner described below. The bolsters 44 and 54 are preferably composed of a resilient, medical grade material capable of withstanding repeated cleaning and/or sterilization. For example, the bolsters 44 and 54 can be formed from short segments of medical grade rubber tubing, or from several pieces of tubing interfitting one another with one having an outside diameter generally equal to the inside diameter of a second outer piece of tubing. The bolsters 44 and 54 may have either blunt or tapered longitudinal ends. Tapered ends for the bolsters 44 and 54 are preferred, so as to avoid any sharp edges that could cause damage to the skin or tissue of the penis shaft 14.

The ventral bolster 54 of the preferred embodiment has a somewhat larger outer diameter than the dorsal bolsters 44. For example, the ventral bolster 54 preferably has a 25% to 67% larger outside diameter than the outside diameter of the dorsal bolsters 44. This difference is determined by the fact that the suitable areas 16 between the central dorsal vascular group 20 and the lateral superficial veins 18 are less than the area below the urethra 30 and the corpus spongiosum 32 where pressure is properly applied. Therefore, the diameters of the dorsal bolsters 44 should be less than the diameter of the ventral bolster 54. The diameter of the ventral bolster 54 should be minimized and the length should be maximized to the extent practical, so as to obtain the greatest reduction or stoppage of flow through the urethra 30 while minimizing the ventral pressure (arrow 40) applied by the ventral arm 52. In contrast, the purpose of the dorsal pressure (arrows 38) applied by the dorsal arm 42 is to serve as an overall resistance to the ventral pressure (arrow 40). Since the suitable areas 16 for the application of the dorsal pressure (arrows 38) are less than the area suitable for the application of the ventral pressure (arrow 40), it is preferable to make the dorsal bolsters 44 somewhat longer than the ventral bolster 54. This allows the dorsal pressure (arrows 38) to be kept as low as possible so that excess pressure on the central dorsal vascular group 20 is avoided in case of misalignment of the dorsal bolsters 44, while the ventral pressure (arrow 40) actually needed for adequate closure of the urethra 30 is also minimized.

Forming the bolsters 44 and 54 from medical grade tubing makes it particularly simple to provide for the adjusting movement previously mentioned. Each of the dorsal bolsters 44 in the preferred embodiment includes a slit 62 through which the dorsal arm 42 is received. The material of each bolster 44 presses against the dorsal arm 42 thereby keeping the bolster 44 in a desired position, while at the same time permitting each bolster 44 to be slid along the dorsal arm 42 to precisely locate each of the bolsters 44 over the proper area 16 to which pressure is to be applied. This adjusting movement allows the control device 10 to be custom fit to a particular patient. The ventral bolster 54 can include a comparable slit 64 through which the ventral arm 52 is received in a similar manner.

The slits 62 and 64 may, but need not, pass through the diametric center of the bolsters 44 and 54, respectively. Instead, the arms 42 and 52 are preferably biased away from the penis shaft 14 by having the slits 62 and 64 pass through the bolsters 44 and 54 at a location beyond the diametric center of the bolsters 44 and 54. By having the slits 62 and 64 beyond the diametric center, the arms 42 and 52 are less likely to contact and possibly harm the penis shaft 14. Further, the increased distance between the arms 42 and 52 and the penis shaft 14 allows the bolsters 44 and 54 to provide an increased amount of compressible material therefore improving the comfort and providing a more uniform pressure distribution.

Figure 4:
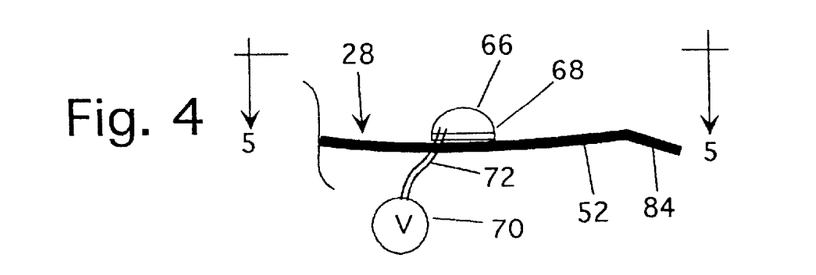
FIG. 4 is a side view of a portion of another preferred embodiment of the present invention.
Figure 5:
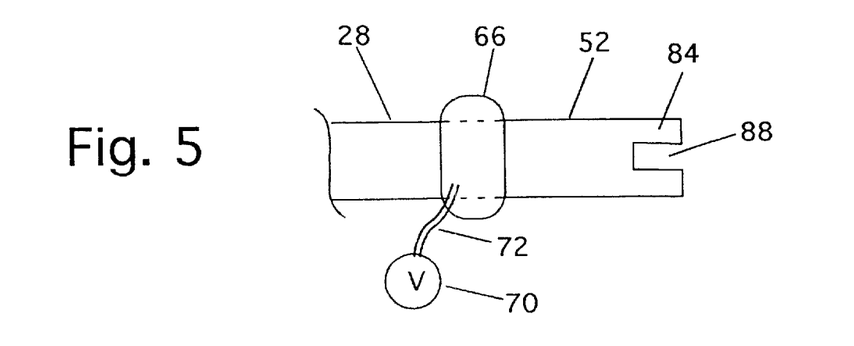
FIG. 5 is a top view of the portion of the preferred embodiment of the present invention shown in FIG. 4.

Referring to FIGS. 4 and 5, another preferred embodiment of the present invention is shown to include a ventral bolster 54 having an inflatable sac 66. The sac 66 can be secured to the ventral arm 52 in a wide variety of ways. In the present embodiment, the sac 66 is detachably secured to the ventral arm 52 by a hook-and-loop type fastener 68. The fastener 68 readily permits precise positioning of the inflatable sac 66 beneath the urethra 30 and corpus spongiosum 32. Preferably, a length of the loop portion of the fastener 68 is secured to the ventral arm 52 thereby allowing an appropriate range of adjustability, while the hook portion of the fastener 68 is secured to the sac 66. This arrangement is preferred since any exposed loop portion is less likely than the hook portion to harm the penis shaft 14.

The inflatable sac 66 can be similar to or identical to the inflatable sac (25) disclosed in the previously referenced U.S. Pat. No. 4,800,900 (the '900 patent). The sac 66 is inflated by actuation of a valve 70, shown schematically, connected to the sac 66 by a tube 72. The tube 72 can be similar to or identical to the tube (27) disclosed in the '900 patent. The valve 70 represents any suitable valve structure for supplying and releasing an inflation gas, such as air. However, the valve 70 most preferably represents the entire valve assembly (30) and syringe assembly (50) shown in the '900 patent. The relevant descriptions of these elements in the '900 patent are expressly incorporated herein by reference.

Unlike the sac (25) in the '900 patent, the inflatable sac 66 in the control device 10 of the present invention is oriented so that its longest dimension lies parallel to the urethra 30 and corpus spongiosum 32, rather than perpendicular to them. The inflatable sac 66 may also be somewhat narrower than the sac (25) of the '900 patent. The sac 66 is preferably only slightly wider than the diameter of the urethra 30 and the corpus spongiosum 32. In a typical application of the present invention, the sac 66 is about 1 inch long and about ¼ to ⅜ inch wide. It is also preferred that the sac 66 have a wall profile height which provides for good vertical movement (that is, towards the penis shaft 14) in the central, longitudinal portion of the sac 66 when the sac 66 expands.

Figure 6:
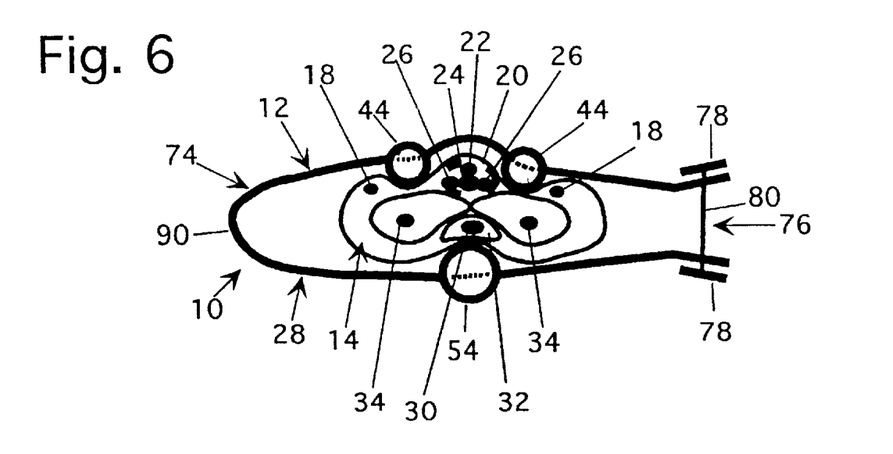
FIG. 6 is a side view of the embodiment in FIG. 1 after application of the device to the penis shaft.

With reference to FIGS. 1, 2, and 6, the incontinence control device 10 is shown to include a spring means 74 connecting the first and second pressure-applying means 12 and 28. It is possible for the spring means 74 to be arranged such that the spring means 74 alone urges the first and second pressure-applying means 12 and 28 towards one another with sufficient force to yield good operation of the control device 10. However, in the preferred embodiment the spring means 74 instead urges the first and second pressure-applying means 12 and 28 apart, and a clip 76 or other limiting element engages the first and second pressure-applying means 12 and 28 and positions the means 12 and 28 to apply a suitable amount of pressure to the penis shaft 14 to control the flow through the urethra 30 (FIG. 6). The clip 76 can, in its simplest form, include a pair of buttons 78 held apart by a rigid wire 80. The buttons 78 engage the first and second pressure-applying means 12 and 28, for example, on angled ends 82 and 84 of the dorsal and ventral anus 42 and 52, respectively. The ends 82 and 84 of the arm 42 and 52 include respective slots 86 and 88 formed therein, through which the wire 80 is disposed. Thus, the clip 76 serves to limit movement of the dorsal and ventral arms 42 and 52 away from each other and therefor away from the penis shaft 14. The wire 80 of the preferred embodiment is rigid so as to make it easier to engage the clip 76 with the first and second pressure-applying means 12 and 28. The length of the clip 76 or the distance between the buttons 78, can be adjusted to control the pressure being applied by the dorsal bolsters 44 and the ventral bolster 54.

The spring means 74 of the present invention is preferably unitarily formed with the first and second pressure-applying means 12 and 28. In the present embodiment, the dorsal and ventral arms 42 and 52 of the first and second pressure-applying means 12 and 28 and the spring means 74 are continuously formed as a generally C-shaped leaf 90. The C-shaped leaf 90 is composed of a suitable material including, but not limited to, metal or plastic. In particular, stainless steel has provided excellent results during testing. The spring means 74 may alternatively be a separate spring (not shown) which connects separate dorsal and ventral arms 42 and 52 to one another.

Figure 7:
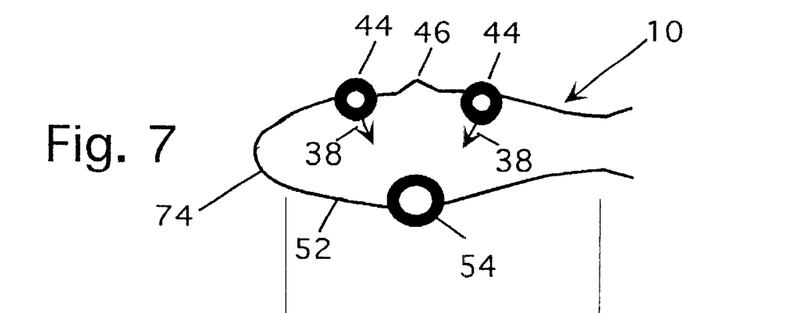
FIG. 7 is a side view of a preferred embodiment made in accordance with the teachings of the present invention.
Figure 8:
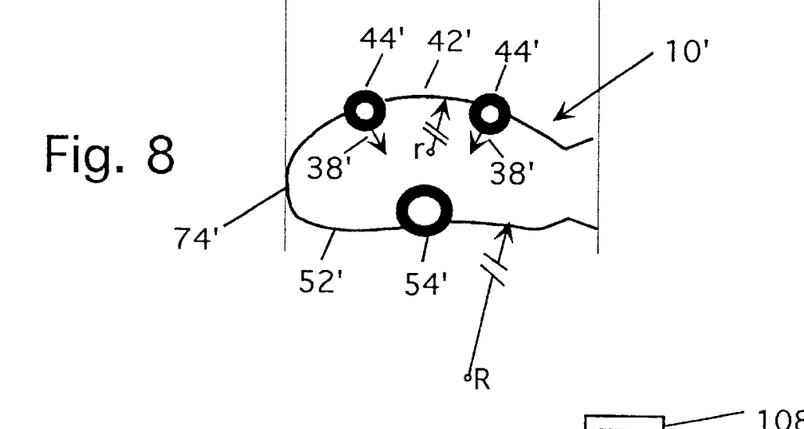
FIG. 8 is a side view of another preferred embodiment made in accordance with the teachings of the present invention.

Referring to FIGS. 7 and 8, a comparison is shown between two preferred embodiments made in accordance with the teachings of the present invention. FIG. 7 shows the control device 10 generally disclosed throughout the description to this point. FIG. 8 shows an alternate embodiment of the control device 10' which is narrower than the control device 10 of FIG. 7. The readers attention is first directed to the arcuate shape of the dorsal arm 42'. The arm 42' provides a radius of curvature "r" which effectively eliminates the need to provide the relief means 46 of the control device 10. The radius of curvature "r" also allows the effective hinge point of the spring means 74' to shift downward toward the ventral bolster 54' when compared to that of the control device 10. Further, the ventral arm 52' of the device 10' also provides an arcuate shape which is in the same direction as that of the dorsal arm 42'. The radius of curvature "R" of the ventral arm 52' is preferably greater than the radius of curvature "r" of the dorsal arm 42'. The configuration of the device 10' as presented allows for a narrower overall width of the control device while still providing sufficient adjustability to accommodate different diameters of the penis shaft 14 (not shown).

An additional advantage of the control device 10' which results from the lowered effective hinge point and from the unique arcuate curvature of the arms 42' and 52' as described, is that the pressure applied by the dorsal bolsters 44 and indicated by the arrows 38' is rotated to direct the resultant force more directly toward the urethra 30. Experimental use of the control device 10' has thus far provided improved comfort and the ability to wear the device 10' for an even g-greater period of time without discomfort. One skilled in the art will readily recognize that modifications and alterations to the particular radii of curvature, "r" and "R", may be required or desirable to provide a series or family of different sized control devices 10' which will be most effective and comfortable to a variety of patients.

Use of the control device 10 of the present invention for controlling male urinary incontinence is relatively straight-forward in light of the present description. In use, it is recommended that the skin of the penis shaft 14 is first covered with a light coating of ointment to protect the skin from prolonged exposure to any urine which may flow past the urethra 30 while wearing the device 10. A 40% zinc ointment or other ointment used to prevent diaper rash is recommended. The skin of the penis shaft 14 is next covered with one or more layers of a flannel or Jersey knit wrap. This knit wrap also protects the penis shaft 14 from the edges 56 and 58 of the dorsal and ventral arms 42 and 52 of the device 10, and helps to retain the cross section of the penis shaft 14 in a reasonably normal shape before application of the device 10.

In addition, one or more layers of "COBAN"® or other similar adhesive wrap material can be applied as a bandage wrap to further maintain the cross sectional shape of the penis shaft 14, and to provide a gripping surface for the bolsters 44 and 54 to work against. The adhesive wrap also helps maintain the location of the bolsters with respect to each other, keep the lower bolster under the urethra and the top two bolsters straddling the central vascular group. The bandage wrap further serves as a partial barrier to urine, protecting the knit wrap and the skin of the penis shaft 14. For simplicity, the ointment, knit wrap, and bandage wrap are collectively designated in FIG. 2 as a single layer of wrap 92.

Next, the dorsal and ventral bolsters 44 and 54 are properly positioned on the dorsal and ventral arms 42 and 52, respectively, if not previously positioned. The clip 76 is opened or removed and the control device 10 is slipped onto the penis shaft 14 from the side. The leading edge of the dorsal arm 42 should be positioned about ¼ inch or more from the rim of the glans (not shown) of the penis shaft 14. With the device 10 held in an approximately correct position with respect to the penis shaft 14, the two dorsal bolsters 44 are moved on the dorsal arm 42 until positioned over the areas 16 between the lateral superficial veins 18 and the central dorsal vascular group 20. This places the dorsal bolsters 44 almost directly over the deep arteries 34 in the corpi cavernosa 36. The ventral bolster 54 is then moved on the ventral arm 52 until it is positioned under the urethra 30 and the corpus spongiosum 32. Proper positioning is checked visually. For example, the patient can rotate the penis shaft 14 upward and sight down along the length of the shaft 14 to determine the precise orientation of the device 10. This is particularly important with regard to the position of the ventral bolster 54.

The proper positioning of the ventral bolster 54 in the above embodiments should be considered to be critical to the successful use of the control device 10. There is very little tolerance for misalignment since leakage flow through the urethra 30 will vary in direct proportion to any degree of misalignment. The patient should be reminded of this, but should also be advised that there will be an initial learning curve for the proper positioning of the ventral bolster 54. A visible indicator can be used to mark the proper locations of the bolsters 44 and 54 on the dorsal and ventral arms 42 and 52 once the proper locations have been established. Some subsequently discussed embodiments disclose designs not requiring such precise locating of the vertical bolster.

The ends 82 and 84 of the arms 42 and 52 are then squeezed together in the direction of arrows 94 (FIG. 2) to allow engagement of the clip 76 in the slots 86 and 88. This action results in pressure being applied by the bolsters 44 to the areas 16 in the direction of the arrows 38, and pressure being applied by the ventral bolster 54 to the urethra 30 and the corpus spongiosum 32 in the direction of the arrow 40, thereby preventing any leakage or any substantial leakage of urine through the urethra 30.

This description of the procedure for using the control device 10 of the present invention may make such use appear to be a bit cumbersome. However, the procedure in fact takes only a few minutes to accomplish. It readily becomes second nature to the patient, and is a small price to pay for the comfort, security and convenience which the device 10 provides.

More particularly, urination while wearing the control device 10 is simple. If the ventral bolster 54 is other than the inflatable sac 66 (previously described and shown), the clip 76 is disengaged from the slots 86 and 88 and releases the ends 82 and 84 of the arms 42 and 52, thereby removing pressure applied to the urethra 30 and permitting the flow of urine through the urethra 30. When the bladder is voided, the ventral bolster 54 is again accurately aligned with the urethra 30 and the corpus spongiosum 32, and the clip 76 is reinstalled by the patient. Alternatively, if the device 10 includes a ventral bolster 54 having the inflatable sac 66, the valve 70 is actuated to deflate the sac 66 which permits the flow of urine through the urethra 30 without requiring the device 10 to be opened. Once the bladder is voided, the valve 70 is used to inflate the sac 66 and once again apply pressure in the direction of the arrow 40 thereby closing the urethra 30.

While the present invention has been described in terms of a particular preferred embodiment, one skilled in the art will readily recognize that the principles of the disclosed control device 10 can be applied to a wide variety of other incontinence control devices. Accordingly, the present invention can be considered as a broad improvement in any strap, band, cuff, clamp, or cradle type urinary incontinence control device which is attachable to the penis shaft 14 and which applies pressure ventrally to at least the urethra 30 and the corpus spongiosum 32. More particularly, the improvement consists of providing on a device of this type the previously disclosed first means 12 for applying preferential pressure to the penis shaft 14 at the suitable areas 16 between the lateral superficial veins 18 and the central dorsal vascular group 20, whereby adequate pressure to substantially reduce leakage of urine through the urethra 30 can be applied without unduly interfering with the flow of blood in the penis shaft 14, and without causing pain or trauma to the patient despite wearing the control device 10 for a prolonged period, for example, up to eighteen hours per day on a continuous daily basis.

The male urinary incontinence control device 10 of the present invention is preferably composed of medical grade materials which can be cleaned and/or sterilized by conventional procedures before and after use. Conveniently, the incontinence control device 10 can be made of a variety of relatively inexpensive materials of suitable resiliency and rigidity.

Several practical considerations regarding use and construction of the control device 10 according to the present invention merit mention. When the ventral bolster 54 is not an inflatable sac 66, the clip 76 must be carefully dimensioned to the particular patient using the device 10. In contrast, use of the inflatable sac 66 as the ventral bolster 54 may make it possible to adapt a single size of the control device 10 to a variety of patient sizes. This of course requires the sac 66 to be inflatable over an adequate range of volumes and/or heights.

Further, the clip 76 need not be a separate piece but can be hinged or captured at one end to one of the dorsal and ventral arms 42 and 52. The clip 76 can also be adjustable in length, for example, by having a threaded rod or post in place of the wire 80, and a threaded wheel or nuts in place of one of the buttons 78. The end of the rod or post can be peened or capped to prevent loss of the wheel by inadvertent threading of the wheel free of the post. One particular embodiment of the device as just described is shown in FIGS. 9 and 10.

Figure 9:
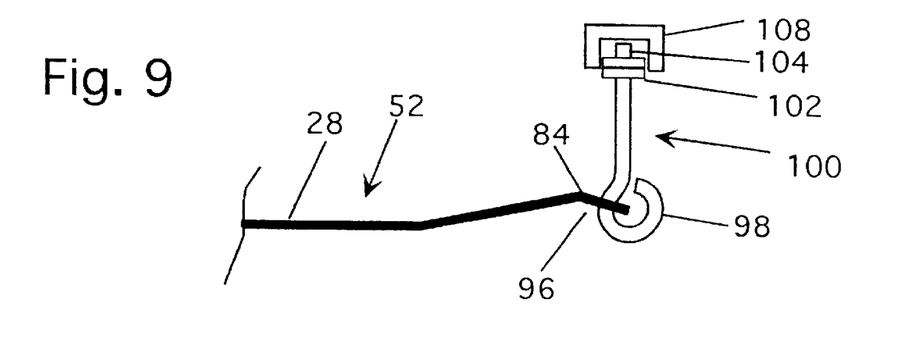
FIG. 9 is a side view of a further preferred embodiment of an adjustable closure means of the present invention.
Figure 10:
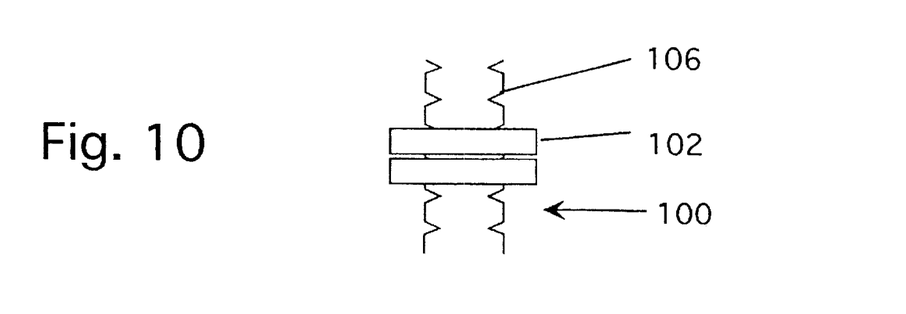
FIG. 10 is a detailed view of a portion of FIG. 9.

FIG. 9 shows a portion of the second pressure-applying means 28, and particularly a portion of the ventral arm 52. A hole 96 is provided at the end 84 of the arm 52 to receive a first end 98 of a threaded fastener 100. The first end 98 of the fastener 100 is designed to be captured on and remain fastened to the arm 52. Locking nuts 102 are threaded on a second end 104 of the fastener 100 and once properly located can be rotated in directions opposite one another such that the nuts 102 axially engage the threads of the fastener 100. This axial engagement locks the nuts 102 in an infinitely variable desired location. Once the nuts 102 have been properly adjusted and locked, the fastener 100 can be shortened by breaking off any excess which extends above the nuts 102. Break-off notches 106 are provided to allow for easy shortening of the fastener 100, as shown in FIG. 10. A cap 108 is placed over the second end 104 of the fastener 100 and may, but need not, completely or partially cover the nuts 102. The cap 108 in the preferred embodiment is made of a soft plastic material and reduces or eliminates the possibility of causing harm to the penis shaft 14 and improves comfort for the patient when wearing the control device 10.

Figure 11:
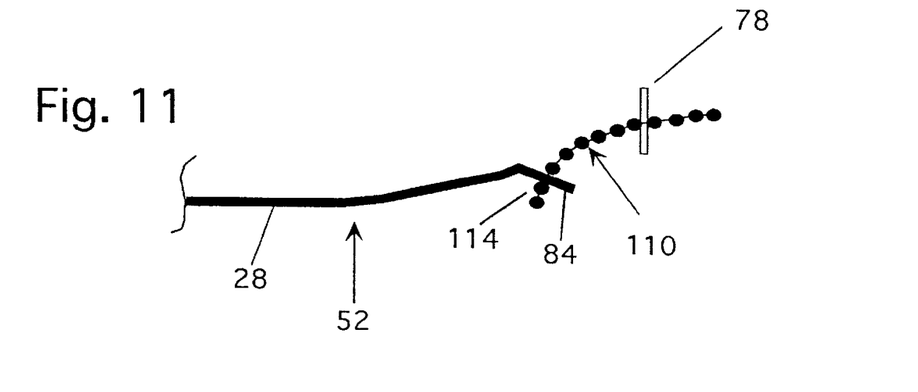
FIG. 11 is a side view of a portion of a preferred embodiment of an adjustable closure means made in accordance with the teachings of the present invention.
Figures 12, 13:
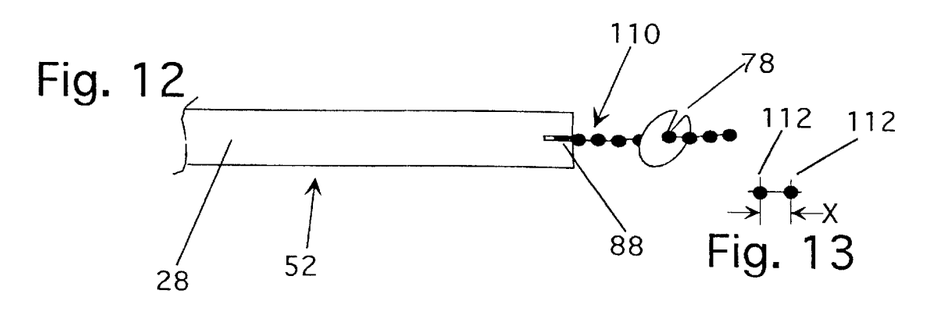
FIG. 12 is a top view of the portion of the embodiment shown in FIG. 11.
FIG. 13 is a detailed view of a segment of FIG. 12.

Referring to FIGS. 11–13, the retaining function of the clip 76 can also be accomplished with a short section of fine stainless steel bead chain 110. The chain 110 includes a plurality of beads having spaces there between. FIG. 13 shows a detailed view of a section of chain 110 wherein adjacent beads 112 provide a spacing indicated as "X". In the preferred embodiment, the spacing "X" is equal to or less than 1/8 inch thereby providing proper incremental adjustment of the control device 10. The degree of closure of the dorsal and ventral arms 42 and 52 is determined by which particular spaces along the chain 110 and between the adjacent beads 112 receives the ends 82 and 84 of the arms 42 and 52 therein. As shown in FIG. 11, one end 114 of the bead chain 110 can be permanently attached to either of the ends 82 or 84 of the dorsal or ventral arms 42 or 52, respectively, to prevent loss of the bead chain 110. Further, the button 78 includes a slot 116 so that the button 78 can be selectively positioned along the chain 110.

Figure 14:
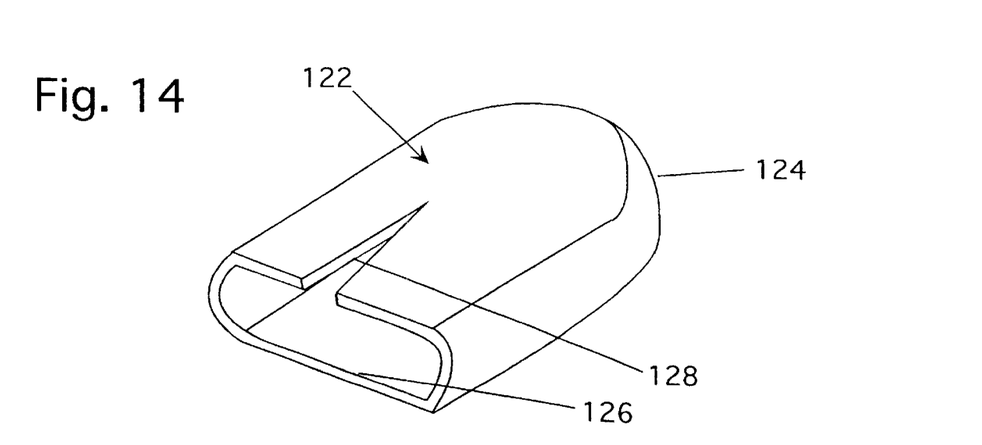
FIG. 14 is a perspective view of another portion of the preferred embodiment of the present invention.

Referring to FIGS. 1 and 14, it is noted that when the control device 10 of the present invention is to be applied to a patient on a long-term basis it may be highly desirable to prevent the end 84 of the ventral arm 52. as well as the button 78 received in the slot 88 in the end 84, from damaging the skin of the scrotum. In a preferred embodiment, a smooth plastic cover 122 is placed over the end 84 of the ventral arm 52 and the associated button 78. The plastic of the cover 122 is preferably soft and flexible, and conveniently can be about 1/16 inch thick. As shown in FIG. 14, the cover 122 is rounded on a first, closed end 124 and includes an opening 126 opposite the closed end 124. The cover 122 also includes a slot 128 extending from the opening 126 to accommodate the wire 80 of the clip 76. The cover 122 covers any sharp edges or corners on the end 84 of the ventral arm 52 or the associated button 78, thereby presenting a completely smooth surface to the skin of the scrotum.

While the dorsal and ventral arms 42 and 52 and the spring means 74 (together formed as the leaf 90) have been disclosed as being preferably composed of stainless steel, a variety of other materials can be utilized as well. More particularly, thermoplastic materials including but not limited to polypropylene, nylon, or acetyl resins are well suited and would permit a variety of different sized devices to be manufactured by injection or other forms of molding at a relatively low cost. The rigidity or stiffness of the spring means 74 can be controlled by modifying the thickness or cross-sectional shape of the leaf 90. Moreover, like stainless steel, the use of plastics such as those disclosed will permit the device 10 to be easily cleaned, and will make the device 10 chemically inert or resistant to urine and to a zinc based or other ointment if used.

A variety of closure mechanisms can be used in place of the clip 76, particularly when the ventral bolster 54 utilizes the inflatable sac 66. The dorsal and ventral bolsters 44 and 54 need not be medical grade latex or rubber tubing, but instead can be a relatively flexible elastomeric material including but not limited to urethane, vinyl, or a low density polyethylene.

It is contemplated that, particularly when the ventral bolster 54 utilizes the inflatable sac 66, the device 10 can be provided to the patient in the form of a kit. Such a kit would include the device 10 as described herein, plus a valve assembly and syringe assembly like those disclosed in the '900 patent. Further, the disclosed kit can include one or more spare valve and syringe assemblies which could be left at home, at a place of work, or in a vehicle to permit actuation of the device 10 without having to removing the device 10 in case the original (and detachable) valve and syringe assemblies become lost or are forgotten.

Figure 15:
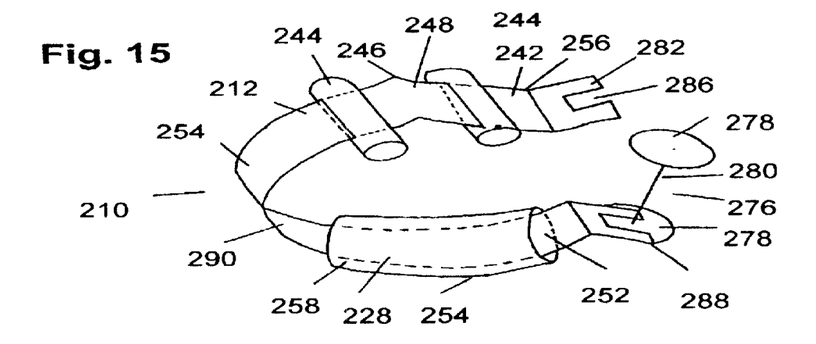
FIG. 15 is a perspective view of another embodiment of the present invention.
Figure 16:
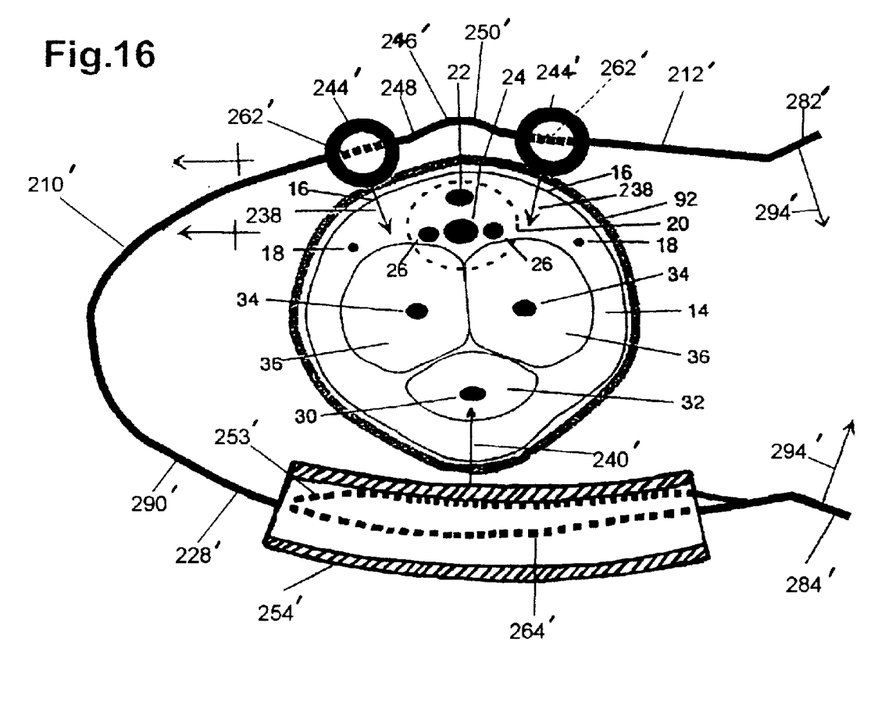
FIG. 16 is a side view of the embodiment of FIG. 15 immediately prior to application of the device to the penis.

Referring now to FIGS. 15 and 16, a male urinary incontinence control device 210, according to another embodiment of the present invention, is illustrated therein. The control device 210 includes a first means 212 for applying preferential pressure to the penis shaft 14 at area 16 between the lateral superficial vein 18 and the central dorsal vascular group 20. The control device 210 also includes a second means 228 for applying pressure ventrally to the penis shaft 14 at the urethra 30 and corpus spongiosum 32. The first and second pressure-applying means 212 and 228 cooperate to apply sufficient pressure to the penis shaft 14 to substantially close the urethra and prevent leakage, while avoiding the application of undue pressure to the penis shaft 14 at the lateral superficial veins 18, the central dorsal vascular group 20 and the deep arteries 34 in the corpi cavernosa 36. As seen in FIG. 16, the pressure applied dorsally by the first pressure-applying means 212 is designated by arrows 238, while the pressure applied ventrally by the second pressure-applying means 228 is designated by arrow 240.

The first pressure-applying means 212 preferably include a dorsal arm 242 and a pair of spaced apart dorsal bolsters 244 which may be movably carried on the dorsal arm 242. These dorsal bolsters 244 are similar to or the same as those previously discussed in connection with FIGS. 1 and 2 and therefore the prior discussion should be referred to in that regard.

The second pressure-applying means 228 preferably includes a ventral arm 252 and a ventral bolster 254 which may be movably carried on the ventral arm 252. The ventral bolster 254 faces and projects towards the first pressure-applying means 212. In this embodiment, however, the ventral bolster 54 is oriented so as to be transverse to the penis shaft 14 and urethra 30 when the device 210 is applied to the penis shaft 14.

As discussed above in connection with dorsal bolsters 44 and the ventral bolster 54 of the embodiment seen in FIGS. 1 and 2, the bolsters 244 and 254 can be formed in any convenient shape suited to provide the pressures indicated above. Additionally, the ventral bolster 254 is generally formed so as to be firmer than the penis shaft 14 with the dorsal bolsters 244 being equal to or softer than the penis shaft 14. Further details regarding the materials of construction for the bolsters 244 and 254 as well as for the wrapping of the bolsters are as discussed previously in this detailed description. Reference thereto should be made in that regard.

Preferably, but not necessarily, the dorsal arm 242 and the ventral arm 252 are each formed with edges 256 and 268 which are angled to ramps from a normal plane 260 of the arm and as generally shown previously in FIG. 3. The edges 256 and 258 are again angled to prevent injury to the penis shaft while applying or wearing the control device 210.

Referring now to FIG. 16, as will be appreciated from a review of the drawing in FIG. 15, the present and subsequent embodiments include numerous elements which are the same or analogous to elements discussed in the prior embodiments. To avoid repetition and undue length in this description, these elements bear reference numbers which correspond with the reference numbers used previously except that they are 200 series designation or higher. For example, the spring means 74 illustrated in FIG. 1 corresponds with the spring means 274 illustrated in FIG. 15. Similarly, the rigid wire 80 of FIG. 1 corresponds to the rigid wire 280 of FIG. 15. Concerning these like elements, the reader is directed to refer back to the prior portions of the discussion regarding prior embodiments. The present sections should then be reviewed, bearing in mind the 200 and higher series designation for the present and subsequent embodiments. Where the present and subsequent embodiments differ from the prior embodiments, specific notation in this discussion will be made.

Figure 17:
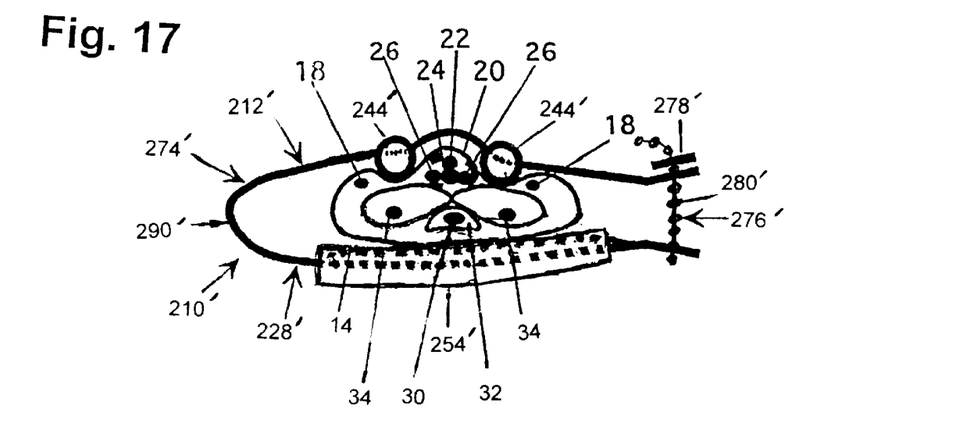
FIG. 17 is a side view like FIG. 16 after application of the device to the penis.
Figure 18:
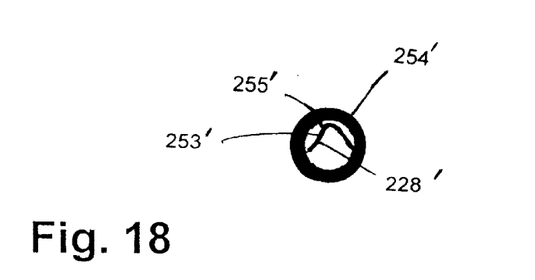
FIG. 18 is a sectional view through the lower pressure-applying means of the device seen in FIGS. 15–18.

Referring now to FIG. 16, the embodiment of FIG. 15 is illustrated therein with one modification. The ventral arm 252', of the second pressure-applying means 228', is provided with a modified shape from the flat cross section seen in FIG. 15. More specifically, the cross-sectional shape of the ventral arm 252' is provided with an inverted "V-shape" as generally seen in FIG. 18. This inverted V-shaped cross-sectional shape is hereafter referred to as a "projection" 253'. Notably, the apex or point 255' of the projection 253' is toward the penis shaft 14. It is believed that the incorporation of the inverted V-shaped projection 253' on the ventral arm 252' will allow for a much lighter pressure to be used with the device 210' in order to stop urine flow. In addition, by modifying the lower bolster 254' so that it is oriented transversely to the penis shaft 14, the critical location of the ventral bolster 254', with respect to the urethra 30, is eliminated. All the user would have to do would be to align the upper bolsters 244' to straddle the central vascular group 20 while not closing the lateral superficial veins 18. Installing the device 210' as such would be relatively easy since the top of a penis is easy to view and the device 210' can be properly applied to the penis only by viewing the penis from above. Additionally, with the location of the lower bolster 254' not being critical with respect to the urethra, the possibility exists to eliminate the adhesive wrap discussed above with prior embodiments as being positioned about each of the bolsters. A device 210', according to the embodiment illustrated in FIG. 16, is illustrated in FIG. 17 properly applied to the penis shaft 14. FIG. 18 shows a cross-sectional view through the ventral arm 252', projection 253' and bolster 254' of the device 210' of FIG. 16.

Referring now to FIGS. 19A and 19B and 20A and 20B are further embodiments of the present invention as illustrated therein. The control device 310 includes a first means 312 for applying preferential pressure to the penis shaft 14 at an area between the lateral and superficial vein 18 and the central dorsal vascular group 20. The control device 310 also includes a second means 328 for applying pressure ventrally to the penis shaft at the urethra 30 and corpus spongiosum 32. The first and second pressure-applying means 312 and 328 cooperate to apply sufficient pressure to the penis shaft 14 to substantially close the urethra 30 and prevent leakage while avoiding the application of undue pressure to the lateral superficial veins 18, the central dorsal vascular group 20 and the deep arteries 34 in the corpi cavernosa 36.

Figure 19A:
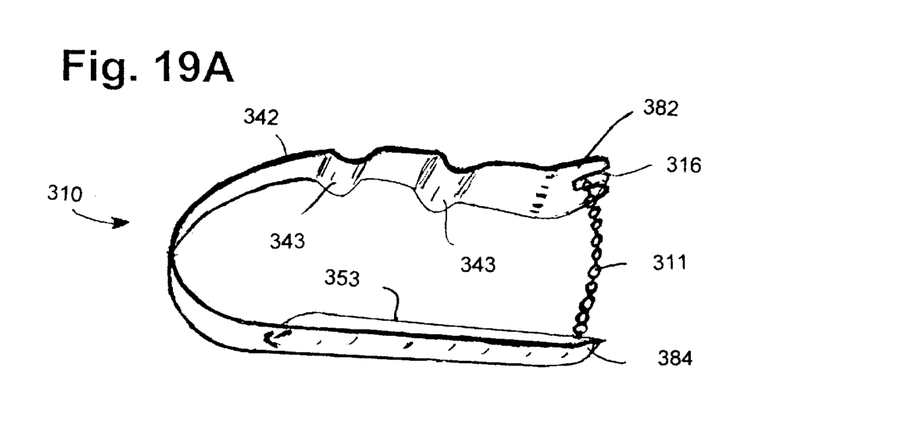
Figure 19B:
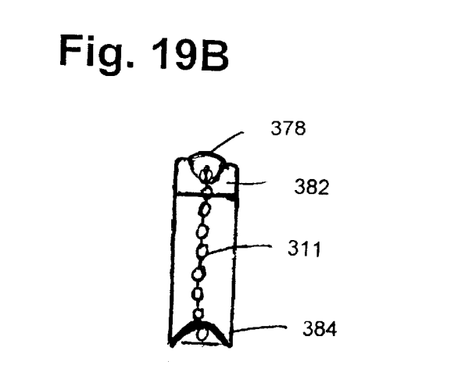

The first pressure-applying means 312 includes a dorsal arm 342 and a pair of spaced apart dorsal bolsters 344. The dorsal bolsters 344 are comprised of a combination of elements and each includes a dorsal projection 343 formed in the dorsal arm 342 over which is received a dorsal pad 345. The dorsal projections 343 are spaced apart from one another along the length of the dorsal arm 342. The dorsal projections 343 are illustrated as generally hemispherical indentations into the dorsal arm 342 and are oriented transversely to the length of the dorsal arm 342. Accordingly, the projections 343 project in a direction toward the application of force by the first pressure-applying means 312. While illustrated as being oriented transversely to the direction of the dorsal arm 342 and as extending completely thereacross, it is noted that other shapes and orientations for the dorsal projections 343 could be utilized. For example, the projections 343 could be provided as hemispherical projections wholly contained within the lateral dimensions of the dorsal arm 342.

Figure 20A:
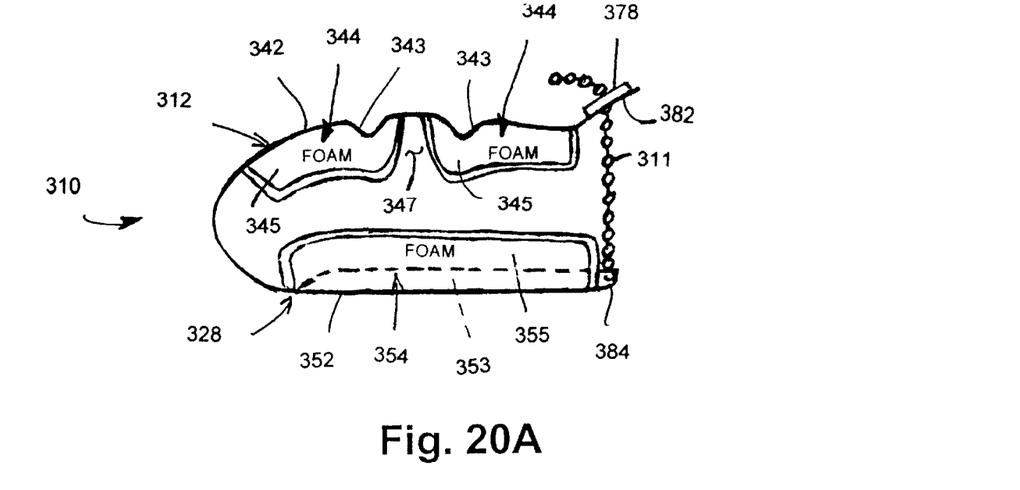
FIG. 20A is a side view of the device seen in FIG. 19A having foam applied to the first and second pressure-applying means thereof and covering the projection of the lower arm.

The dorsal pads 345, seen in FIG. 20A, are adhesively or otherwise secured to the underside of the dorsal arm 342 so as to extend over the dorsal projections 343. The dorsal pads 345 are provided as separate elements spaced apart from one another along the dorsal arm 342. The pads 345 are formed of a closed or open cell foam or other material having the characteristics discussed above in connection with the prior embodiments. Alternatively, the pads 345 could be provided as a unitary pad so long as corresponding with the space 347 between the illustrated pads 345 is provided therewith. The lateral edges 349 of the dorsal pads 345 are chamfered or beveled to prevent injury to the penis shaft while applying or wearing the control device 310.

The second pressure-applying means 328 includes a ventral arm 352 and a ventral bolster 354. The ventral bolster 354 is comprised of a ventral projection 353 and a ventral pad 355. The ventral projection 353 is a V-shaped projection as discussed in connection with the embodiment of FIG. 16 and that discussion is herein incorporated by reference. The ventral pad 355 is adhesively or otherwise secured to the ventral arm 352 over the ventral projection 353. The length of the ventral pad 355 is substantially the same as the length of the ventral arm 352. As with the dorsal pads 345, the edges 359 of the pad are chamfered.

Figure 20B:
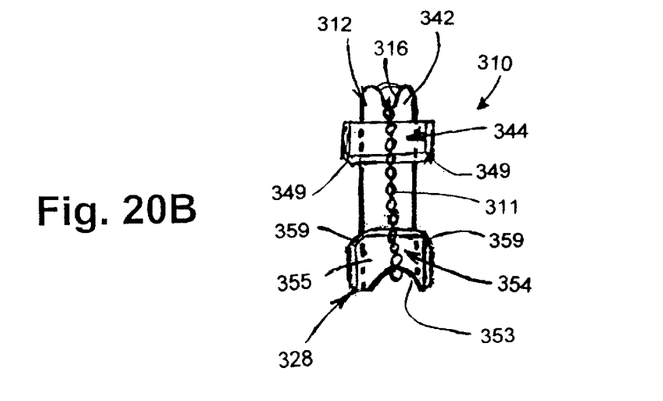
FIG. 20B is an end view of the device seen in FIGS. 19–20B after application to the penis.

Additionally as seen in FIG. 20B, the width of the pads, both the dorsal pads 345 and the ventral pad 355 is wider than the underlying arms 342 and 352. When applied to the penis, this overhang of the pads 345 and 355 further prevents injury to the penis.

Figure 21:
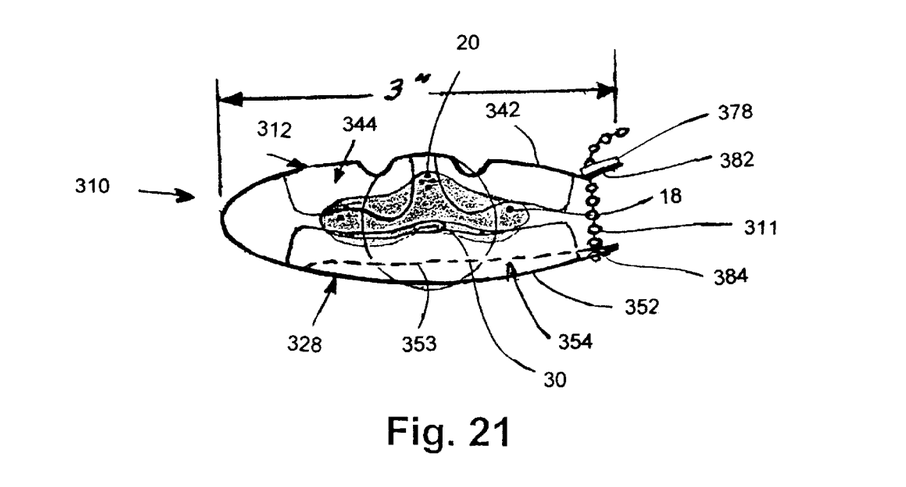
FIG. 21 is a schematic illustration of a modified device similar to that in FIGS. 19 and 20, applied to a penis.

Application of the device 310 to the penis is generally illustrated in FIG. 21. As seen in the figure, under application of pressure to the central vascular group 20 and the lateral superficial veins 18, is avoided while the urethra 30 is occluded to prevent leakage therefrom.

FIG. 21 illustrates the retaining of the device 310 to the penis through use of a bead chain 311 that is permanently attached to an end 382 or 384 of either the dorsal or ventral arm 342 or 352 with a button 378 attached to the chain 311 and engageable with a slot 316 in the opposing arm 382 or 384 so as to selectively retain the device 310 in its closed position. As mentioned previously with respect to prior embodiments, the button is provided so as to be selectively positionable along the chain 311.

Figure 22A:
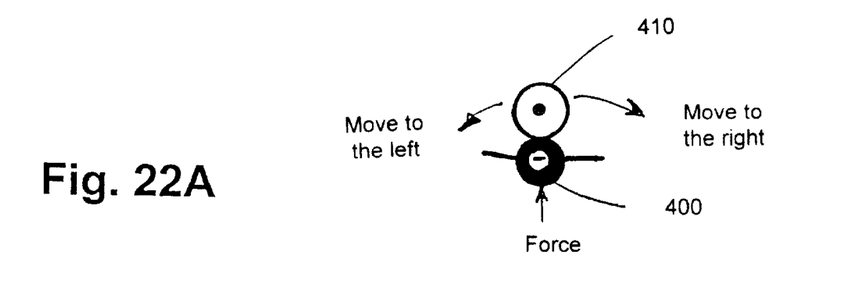
FIGS. 22A–22D illustrate situations where the second pressure means of prior designs has shifted and is off-set from the urethra.
Figure 22B:
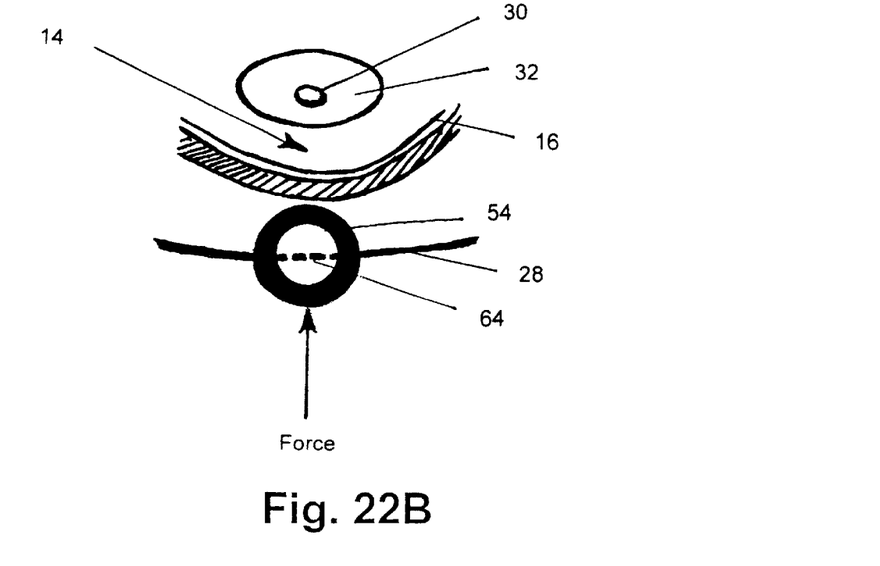
Figure 22C:
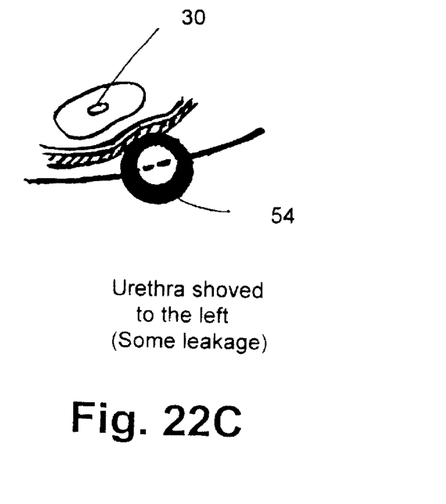
Figure 22D:
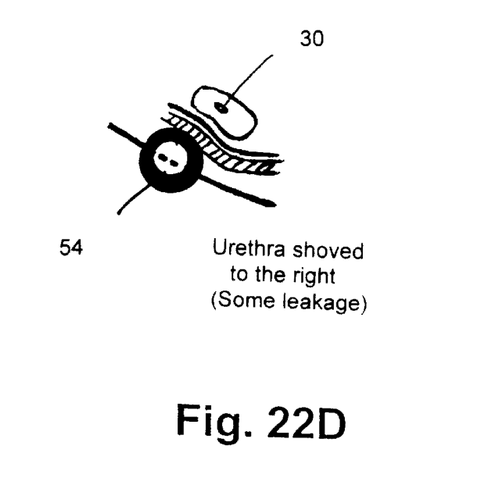

Referring now to FIGS. 22A–22D. illustrated therein is the proper positioning of the longitudinal lower bolster of the earlier embodiments with respect to the urethra and misapplication thereof. FIG. 22A is diagrammatic illustration of the application of the longitudinal lower bolster to the urethra. In this figure, the longitudinal lower bolster is represented by the circle designated at 400 while the urethra is illustrated as this circle designated at 410. Upon the application of force to the urethra 410 from the bolster 400, it is easily seen that misapplication of force by the bolster to the urethra will tend to move the urethra either to the left or to the right. As such, the urethra will not be properly occluded and the device may not work as intended. FIG. 22B illustrates a longitudinally oriented ventral bolster 54 (oriented with the shaft of the penis) and aligned with the urethra where upon clamping of the device may not occlude and close the urethra 30. FIG. 22C illustrates the urethra shifted to the left of the longitudinal ventral bolster 54 while FIG. 22D illustrates the urethra shifted to the right of the ventral bolster 54. In both of the latter figures, some leakage would occur.

With the transverse orientation of the embodiments seen in FIGS. 17–20B (and FIGS. 23A and 23B discussed below), all of these misalignment problems are avoided and alignment of the penis and urethra with respect to the lower bolster is not critical, the device is easier to install and achieves less leakage.

Figure 23A:
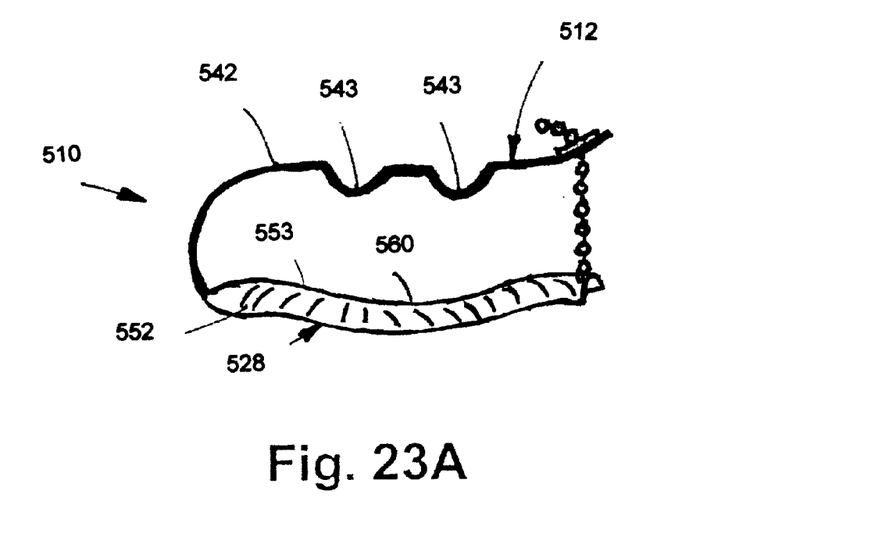
FIGS. 23A and 23B are side views of yet another embodiment of the present invention.
Figure 23B:
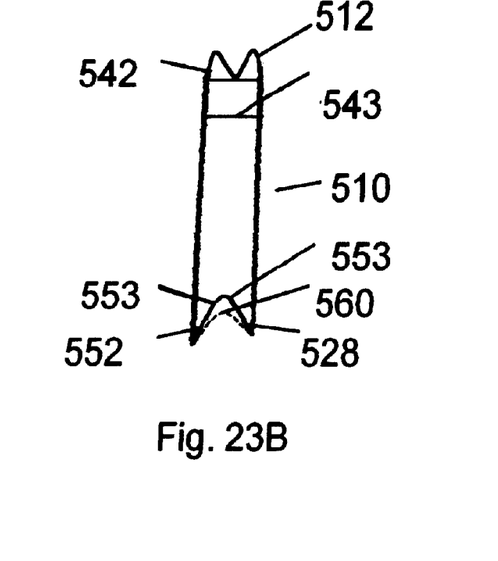

In a final embodiment of the invention, seen in FIGS. 23A and 23B, the ventral arm 552 of the second pressure-applying means 528 is provided with a curvature designed to cradle, position and center the penis in the device 510, relative to the dorsal arm 542 and the projections 543 and bolsters 544. For clarity, the pads are not shown in this embodiment but would be employed in actual use. This curvature is generally concave when viewed from above and provides the ventral arm 552 with a central depression 560 beneath the bolster 544 of the dorsal arm 542. The dorsal arm 542 itself is of the same constructions as provided in the embodiment illustrated in FIG. 19A while the ventral arm of that embodiment is modified with the curvature and depression 560 mentioned above. The ventral arm 552 continues to contain a ventral projection 553, which is of the construction and shape mentioned with the previous embodiment. Specifically, the projection 553 has an inverted V-shaped cross-sectional shape with its apex pointing toward the dorsal arm 542.

Finally, while it is expected that the incontinence control devices 10, 210 and 310 of the present invention will prevent the leakage of up to as much as 94–99% of a patient's daily urine output, this still leaves a small but appreciable amount of urine that needs to be dealt with. This small amount of leakage can readily be captured by either a small absorbent pad or a small diaper simply opened and placed inside the under garments to cover the end of the penis. Experimental use of the control devices 10, 210 and 310 of the present invention has demonstrated that such leakage is so limited that a small diaper can work properly for several days. The pads used in conjunction with the device 10 can be much smaller than the large pads and diapers conventionally used for the complete capture of urine, and are much easier to use.

It should be clear from the foregoing disclosure that the incontinence control device 10 of the present invention is particularly advantageous in a variety of ways. Most importantly, the present invention is advantageous in that it avoids applying undue pressure to the lateral superficial veins and the central dorsal vascular group while ensuring that sufficient pressure is applied to the urethra and the corpus spongiosum to prevent or substantially reduce leakage through the urethra. The disclosed positioning of the dorsal pressure-applying means unexpectedly avoids the application of undue pressure to the deep arteries in the corpi cavernosa, even when the applied pressure is sufficient to close or substantially close the urethra. The discomfort experienced during use of the device is thereby lowered. The present invention permits a relatively precise selection of the dorsally and ventrally applied pressures by adjustment of the spring means, the curvature of the dorsal arm, and the selection of the length of the clip or closure means, if present. The present control device substantially avoids the pain. trauma and/or damage to the skin and underlying tissues of the penis experienced during the use of other devices of this type such that the device can be comfortably worn by the patient for an entire day. The control device of the present invention is relatively inexpensive in construction, is relatively easy to properly position on the penis, and is relatively easy to remove for urination. Indeed, when the device incorporates an inflatable sac of the type disclosed in U.S. Pat. No. 4,800,900, instead of a bolster or pad, the device need not be removed even during urination.

While the various embodiments are illustrated and discussed herein, it is noted that those embodiments where the lower bolster or pad is oriented transverse to the penis shaft and urethra are preferred. Applicants have found that the transverse orientation of the present invention offers several advantages including: 1) alignment with the urethra is no longer critical, 2) ease of use and application is increased and 3) leakage is reduced, by at least a factor of two.

The details of the construction or composition of the various elements of the incontinence control devices 10, 210 and 310 of the present invention not otherwise disclosed are not believed to be critical to the achievement of the advantages of the present invention, so long as the elements possess the strength or flexibility needed for them to perform as disclosed. The selection of any such details of construction are believed to be well within the ability of one having skill in this area, in view of the present disclosure.

The present invention is useful as a medical appliance for controlling male urinary incontinence, and therefore finds applicability in human and veterinary medicine. It is to be understood, however, that the above-described device is merely an illustrative embodiment of the principles of this invention, and that other devices and methods for using them may be devised by those skilled in the art, without departing from the true spirit and fair scope of the present invention as defined in the following claims.

What is claimed is:

1. A male urinary incontinence control device comprising:

first means for applying preferential pressure to the penis shaft at areas between the lateral superficial veins and the central dorsal vascular group, the first pressure-applying means including a dorsal arm; and second means for applying pressure ventrally to the penis shaft at the urethra and the corpus spongiosum, the second pressure-applying means including a ventral arm and ventral bolster located on the ventral arm and facing the first pressure-applying means, the ventral arm has a ventral projection formed thereon and projecting in a direction toward the first pressure-applying means, the projection is covered by the ventral bolster the ventral bolster being oriented along the length of the ventral arm and transverse to the penis shaft.

2. A male urinary incontinence control device comprising:

first means for applying preferential pressure to the penis shaft at areas between the lateral superficial veins and the central dorsal vascular group, the first pressure-applying means including a dorsal arm; and second means for applying pressure ventrally to the penis shaft at the urethra and the corpus spongiosum, the second pressure-applying means including a ventral arm and ventral bolster located on the ventral arm and facing the first pressure-applying means, the ventral arm having a ventral projection formed thereon and projecting in a direction toward the first pressure-applying means, the projection is generally an inverted V-shape in cross-section having its apex toward the first pressure-applying means, the ventral bolster being oriented along the length of the ventral arm and transverse to the penis shaft.

3. A male urinary incontinence control device comprising:

first means for applying preferential pressure to the penis shaft at areas between the lateral superficial veins and the central dorsal vascular group, the first pressure-applying means including a dorsal arm; and second means for applying pressure ventrally to the penis shaft at the urethra and the corpus spongiosum, the second pressure-applying means including a vertical arm and vertical bolster located on the ventral arm and facing the first pressure-applying means, the ventral bolster being oriented along the length of the ventral arm and transverse to the penis shaft, the ventral bolster includes chamfered lateral edges.

4. A male urinary incontinence control device comprising:

first means for applying preferential pressure to the penis shaft at areas between the lateral superficial veins and the central dorsal vascular group, the first pressure-applying means including a dorsal arm;

second means for applying pressure ventrally to the penis shaft at the urethra and the corpus spongiosum, the second pressure-applying means including a vertical arm and vertical bolster located on the ventral arm and facing the first pressure-applying means, the ventral bolster being oriented along the length of the ventral arm and transverse to the penis shaft; and retainer means connecting the first and second pressure-applying means and retaining them in a predetermined spaced apart relation, the retainer means is a clip selectively connectable to the dorsal and ventral arms and spring means generally opposite the clip, the clip thereby limiting movement of the dorsal and ventral arms away from one another.

* * * * *